United States Patent
Reichman et al.

(10) Patent No.: US 6,168,762 B1
(45) Date of Patent: Jan. 2, 2001

(54) APPARATUS AND METHOD FOR PRODUCING POROUS SUPERABSORBENT MATERIALS

(76) Inventors: Eliezer Reichman, 29/9 Gordon St., Rehovot 76289; Arkady Skibinsky, 7/8 Ahim Klbovich, Rehovot 76450; Diana Kumin, 17/7 Vinik St., Rishon-le-Zion 75241, all of (IL)

( * ) Notice: Under 35 U.S.C. 154(b), the term of this patent shall be extended for 0 days.

(21) Appl. No.: 09/100,721

(22) Filed: Jun. 19, 1998

Related U.S. Application Data

(62) Division of application No. 08/574,964, filed on Dec. 19, 1995, now Pat. No. 5,859,077.

(51) Int. Cl.[7] .............................. B06B 1/00; B01F 11/00
(52) U.S. Cl. ........................ 422/128; 422/135; 422/224; 366/276; 366/292
(58) Field of Search ..................................... 422/128, 129, 422/133–135, 137, 138; 366/243–244, 276, 279, 292, 341, 342

(56) References Cited

U.S. PATENT DOCUMENTS

| | | | |
|---|---|---|---|
| 3,980,280 | 9/1976 | Benson | 366/150.1 |
| 5,261,746 | * 11/1993 | Boasso | 366/276 |
| 5,328,935 | 7/1994 | Van Phan et al. | 521/64 |
| 5,334,621 | 8/1994 | Beshouri | 521/64 |
| 5,338,766 | 8/1994 | Phan et al. | 521/64 |
| 5,372,766 | 12/1994 | Roe | 521/63 |
| 5,484,573 | * 1/1996 | Berger et al. | 422/128 |

FOREIGN PATENT DOCUMENTS

| | | |
|---|---|---|
| 0295438 | 12/1998 | (EP) . |
| 60-221441 | 11/1985 | (JP) . |
| WO/95/05204 | 8/1994 | (WO) . |

OTHER PUBLICATIONS

Riccardo Po, "Water–Absorbent Polymers: A Patent Survey", Journal of Macromolecular Science, Reviews Macromolecular Chemistry, 1994, C34(4), pp. 607–662.

Timothy J. Mason published by Ellis Hormood Ltd. "Practical Sonochemistry" sec. 4.3 1991.

* cited by examiner

*Primary Examiner*—Hien Tran
(74) *Attorney, Agent, or Firm*—Aquilino, Welsh & Flaxman

(57) ABSTRACT

A method and apparatus for producing a superabsorbent foam is provided. The method includes forming a reaction mixture comprising at least one compound capable of forming a superabsorbent foam, stirring the reaction mixture, applying mechanical waves to the reaction mixture and repeating the stirring and applying a selected number of times thereby forming the superabsorbent foam.

24 Claims, 11 Drawing Sheets

71 — non-compressrd samples
72,73 — samples, compressed at 15 and 150 bars, respectively

APPARATUS AND METHOD FOR PRODUCING POROUS SUPERABSORBENT MATERIALS

CROSS REFERENCE TO OTHER APPLICATIONS

This application is a divisional application of U.S. patent application Ser. No. 08/574,964 filed Dec. 19, 1995, now U.S. Pat. No. 5,859,077, incorporated herein by reference.

FIELD OF INVENTION

The present invention relates to apparatus and a method for forming porous superabsorbent materials generally and more particularly to apparatus and a method for producing superabsorbent foams.

BACKGROUND OF THE INVENTION

Superabsorbent polymeric materials capable of absorbing large quantities of liquids are known in the art and used in many applications, in particular in sick-care and hygienic products such as wound dressings, diapers, adult incontinence pads, sanitary napkins and the like. Prior art methods for producing superabsorbent materials capable of absorbing water are based on the use of highly hydrophilic polymers, such as polyacrylates, polyacrylamides, acrylates and their derivatives, grafted on starch or cellulose. Polymeric molecules are usually crosslinked and form a gel-like three-dimensional network. These methods are described in an article entitled *Water-absorbent polymers: a patent survey*, published in the Journal of Macromolecular Science, Reviews Macromolecular Chemistry, 1994, C34, 607–662.

The water absorbing capacity (WAC) of water-absorbing polymers can be substantially increased by forming pores (preferably open-cell pores) within the polymer matrix. Prior art methods of making porous polymer matrices are based on foaming the reaction mixture before or during the run of polymerization and/or crosslinking reactions using a blowing agent, such as gases or volatile liquids. A method of making superabsorbent polymer foam having improved absorptive properties is described, for example, in U.S. Pat. Nos. 5,328,935 and 5,338,766 to Van Phan et al.

Other prior art approaches for forming porous absorbent materials include crosslinking of a multiplicity of precursor particles into an interparticle macroaggregate (U.S. Pat. No. 5,372,766 to Roe), freezing hydrophilic polymers solutions in the form of prenucleated ice sheets with subsequent freeze-drying (PCT application WO 95/05204 to Schonfeldt et al), carrying out polymerization reactions in conditions of a specific type of high internal phase emulsion (U.S. Pat. No. 5,334,621 to Beshouri).

Prior art methods of preparing highly superabsorbent porous materials, also termed herein superabsorbent foams, having high WAC are deficient in some respects. For example, each of the prior art methods can be applied only to polymers of a definite chemical nature. Also, the possibility of fine controlling the parameters of the porous structure are limited, in particular on scaling up these methods for industrial applications.

SUMMARY OF THE INVENTION

A primary object of the present invention is to provide apparatus and a method for producing superabsorbent foams applicable to a variety of different polymers.

A further object of the present invention is to provide a superabsorbent foam made of any reaction mixture capable of forming a superabsorbent foam and having high absorption capabilities of fluids comprising of both low and high molecular weight components, such as urine and blood, respectively.

Another object of the present invention is to provide superabsorbent foams made from a wide range of synthetic and/or natural polymers, such as collagen.

Yet another object of the present invention is to provide a method for forming superabsorbent foams which includes the application of physical forces to a precursor reaction mixture of the polymer foam.

A further object of the present invention is to provide apparatus for forming superabsorbent foams which includes a novel chemical reactor capable of producing the superabsorbent foams of the present invention on an industrial scale.

According to one aspect of the present invention, the suitable chemical reaction mixtures are exposed to steps of physical treatment in a reactor to produce a superabsorbent foam comprising a branched system of interconnecting pores which form a highly porous structure.

According to another aspect of the invention, the foam properties are controlled by applying mechanical waves of controllable frequency, amplitude and wave form. These waves may be periodic waves, such as sinusoidal waves having frequencies from hundreds of Hz to few dozens of KHz i.e., in the sound and near ultrasound range.

According to a further aspect of the present invention, mechanical waves application is used not only during foam formation and solidification but also at further stages of producing the superabsorbent foams. For example, by applying wave treatment during compression of dry super absorbent foams in order to get it in the form of thin pliable sheets convenient for practical applications, involves additional breakage of partitions between pores of the superabsorbent foam, thus favoring formation of a more extensively branched system of interconnecting pores.

It is yet another object of the present invention to provide apparatus for producing superabsorbent foams operating to expose the entire reaction mixture to the application of mechanical waves.

According to yet another aspect of the present invention, the method for producing superabsorbent foams may also include, apart of or instead of mechanical waves application, the alternation of pressure in the reaction volume of the formed reaction mixture by means of introducing into it a blowing agent under alternating pressure values.

According to the present invention, the application of mechanical waves is not limited to any class of compounds which form the polymeric foam through different mechanisms (e.g., polymerization, gelling, cross-linking, sintering).

There is thus provided, in accordance with a preferred embodiment of the present invention, a method for producing a superabsorbent foam including forming a reaction mixture comprising at least one compound capable of forming a superabsorbent foam, stirring the reaction mixture, applying mechanical waves to the reaction mixture and repeating the stirring and applying a selected number of times thereby forming the superabsorbent foam.

Furthermore, in accordance with a preferred embodiment of the present invention, the compound is collagen.

Furthermore, in accordance with a preferred embodiment of the present invention, applying mechanical waves includes sonicating and the waves are ultra sonic waves. Additionally, it includes sonicating the reaction mixture and the additional mechanical and ultra-sonic waves.

Furthermore, in accordance with a preferred embodiment of the present invention, the method further includes alternating the pressure of the reaction mixture during the step of repeating and applying additional mechanical waves to the formed superabsorbent foam thereby increasing its absorbing capacity.

Furthermore, in accordance with a preferred embodiment of the present invention, the method further includes compressing the superabsorbent foam, thereby increasing its absorbing capacity and reducing its volume.

Furthermore, in accordance with Ea preferred embodiment of the present invention, the superabsorbent foam has a high absorption capacity to protein solutions.

Furthermore, in accordance with a preferred embodiment of the present invention, alternating includes employing a blowing agent under alternating pressure values.

In addition, in accordance with a preferred embodiment of the present invention, there is provided the superabsorbent foam produced by the method described hereinabove.

In addition, in accordance with a preferred embodiment of the present invention, there is provided apparatus for forming a superabsorbent foam which includes a reactor having a reaction chamber therein for receiving a reaction mixture which includes at least one compound capable of forming a superabsorbent foam, a stirring unit for stirring the reaction mixture, means for applying mechanical waves to the reaction mixture and a control unit for repeating the operation of the stirring unit and the energy source a selected number of times thereby forming the superabsorbent foam.

Furthermore, in accordance with a preferred embodiment of the present invention, the stirring unit includes a shaft and at least one blade operating to stir the reaction mixture in the reaction volume.

Furthermore, in accordance with a preferred embodiment of the present invention, the apparatus further includes a receiving chamber for receiving the formed superabsorbent foam.

Furthermore, in accordance with a preferred embodiment of the present invention, the apparatus includes a first piston assembly having at least one piston for displacing the formed superabsorbent foam from a first position within the reactor to a second position within the receiving chamber.

Furthermore, in accordance with a preferred embodiment of the present invention, the piston and the blade are complementary in shape, thereby enabling the piston to displace the formed superabsorbent foam.

Furthermore, in accordance with a preferred embodiment of the present invention, the apparatus further includes a second piston assembly for displacing the formed superabsorbent foam from the receiving chamber to a collection chamber.

Furthermore, in accordance with a preferred embodiment of the present invention, the first piston assembly and the second piston assembly operate at least partly in the same volume.

Furthermore, in accordance with a preferred embodiment of the present invention, the apparatus further includes means for changing the pressure in the reaction volume and for introducing a blowing agent into the reaction mixture.

Furthermore, in accordance with a preferred embodiment of the present invention, the apparatus further includes means for applying Ultra Violet energy into the reaction mixture.

Finally, in accordance with a preferred embodiment of the present invention, a superabsorbent foam substantially including collagen is provided.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Figure 1:
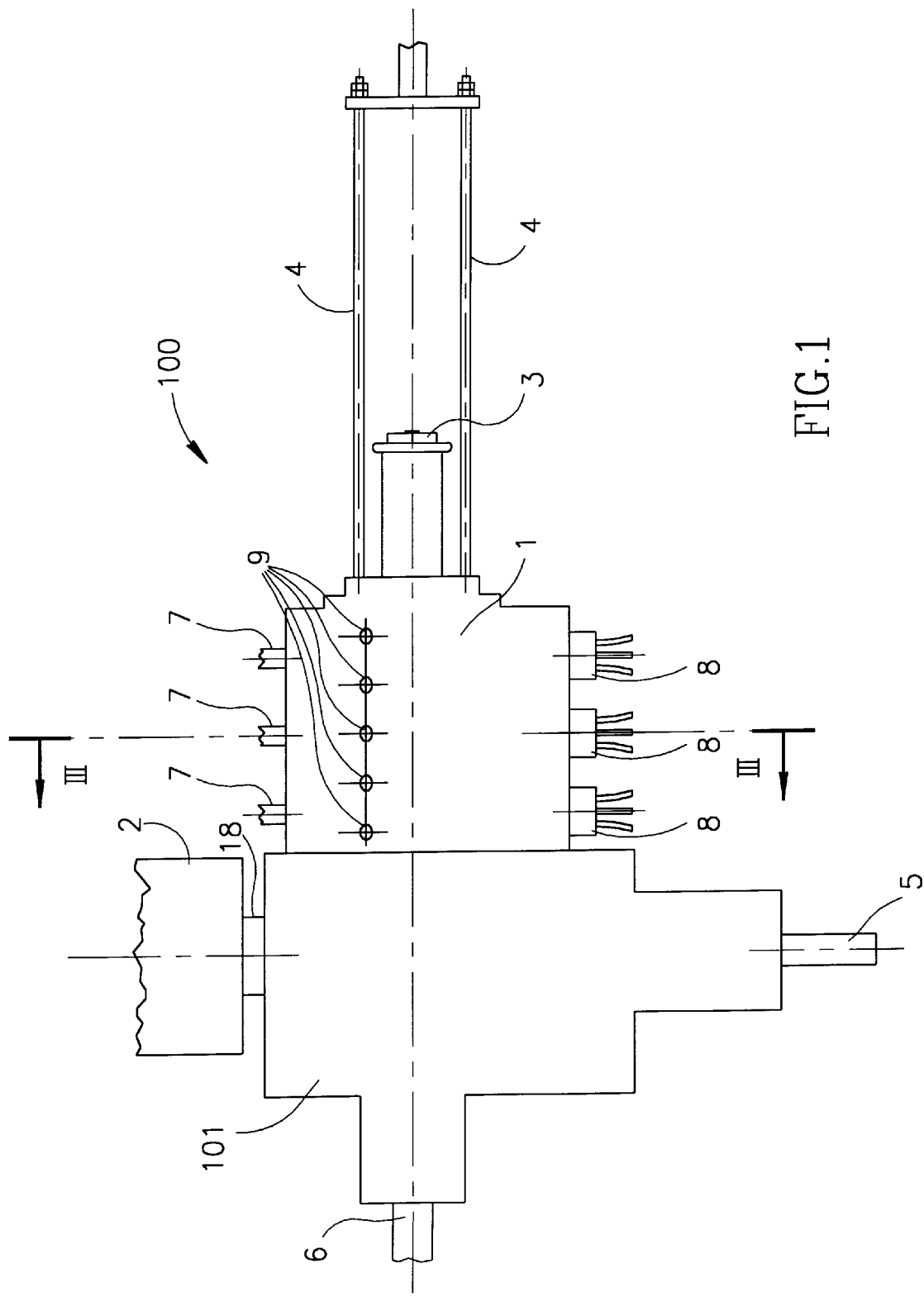
FIG. 1 is a schematic top view illustration of apparatus for producing superabsorbent foams, constructed according to a preferred embodiment of the present invention.
Figure 2:
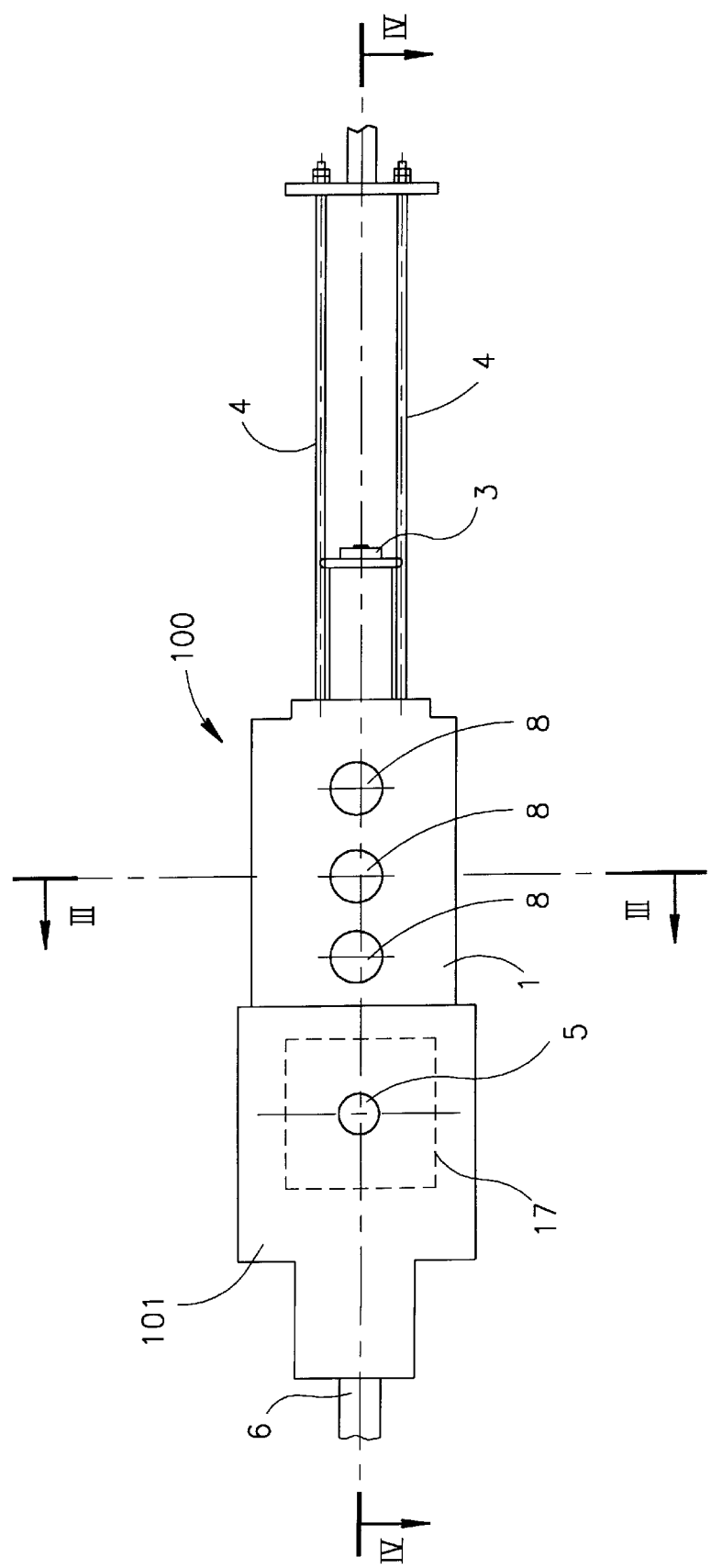
FIG. 2 is a schematic side view illustration of the apparatus of FIG. 1.
Figure 3:
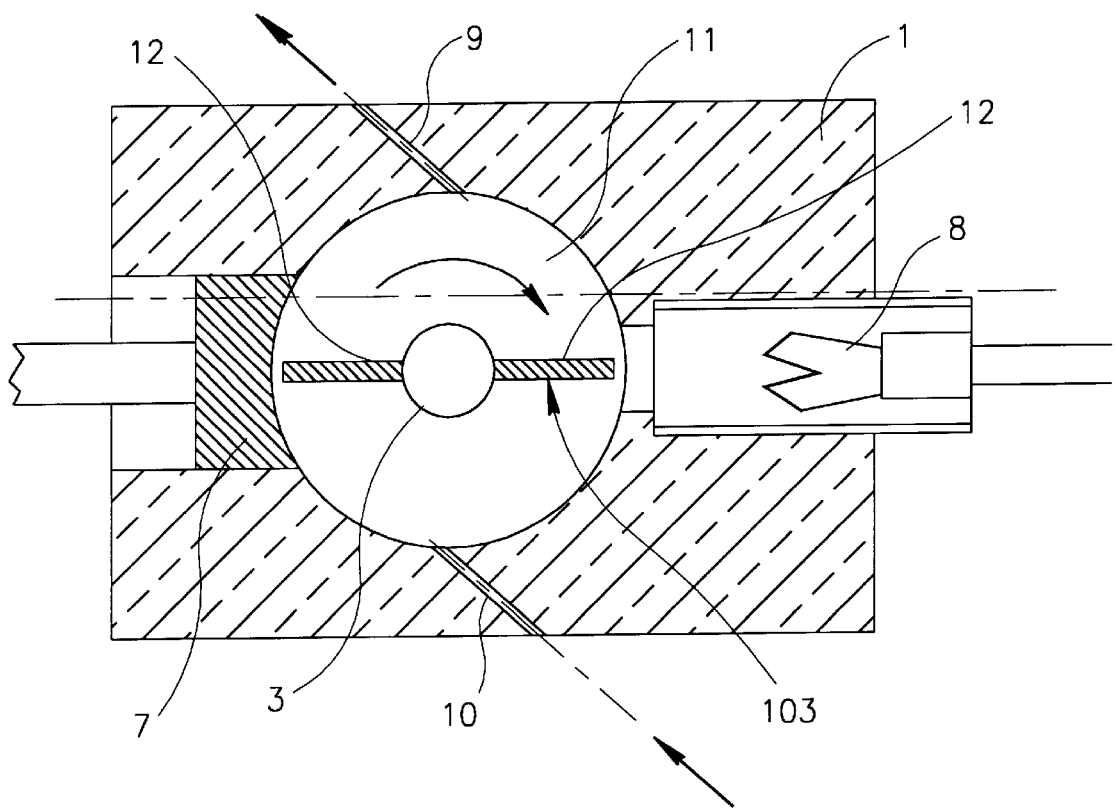
FIG. 3 is a cross sectional schematic view of the apparatus of FIGS. 1 and 2 along lines III—III.
Figure 4:
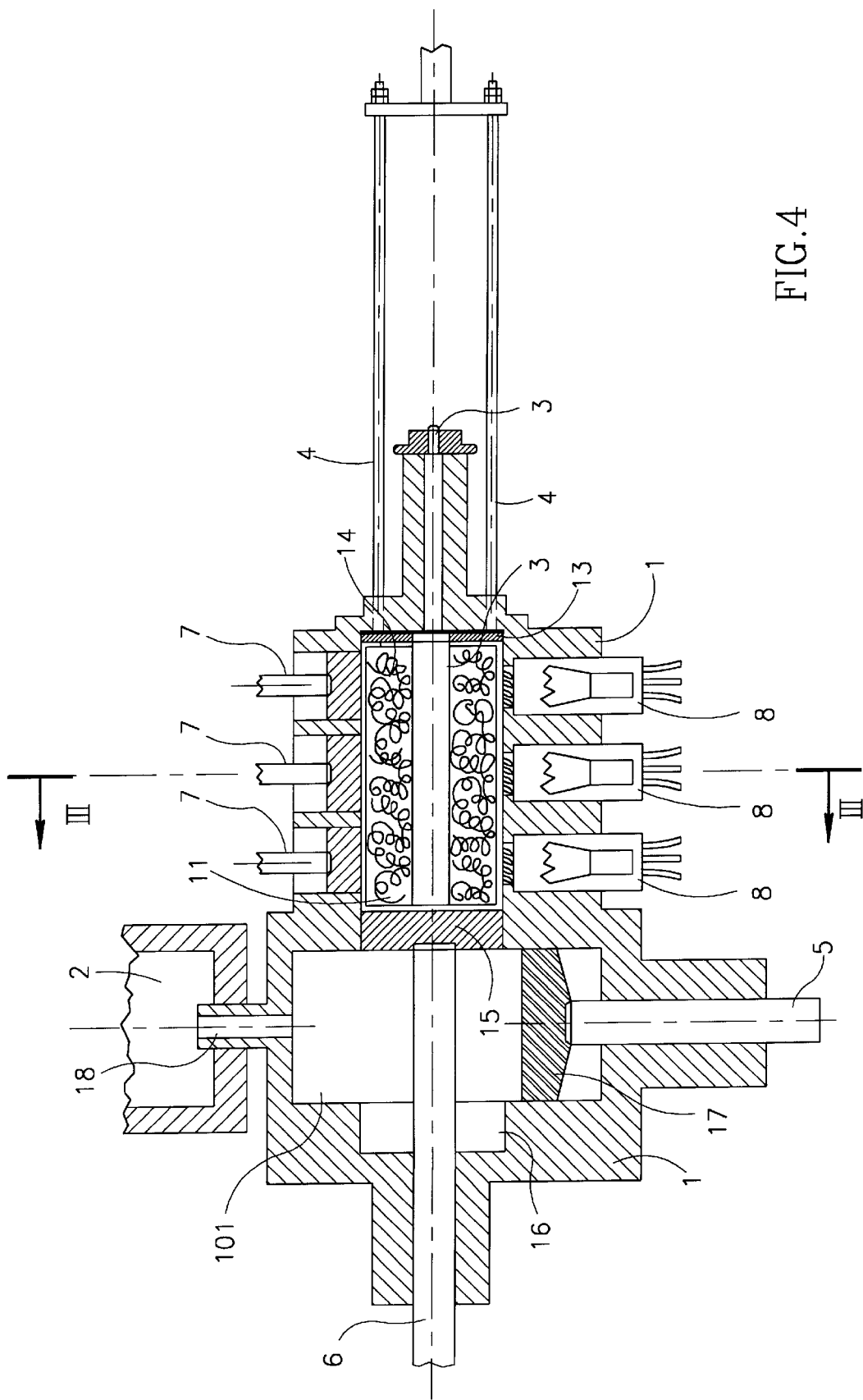
FIGS. 4, 5 and 6 are schematic cross sectional illustrations along lines IV—IV of FIG. 2 illustrating the apparatus of FIGS. 1–3 in three working positions.
Figure 5:
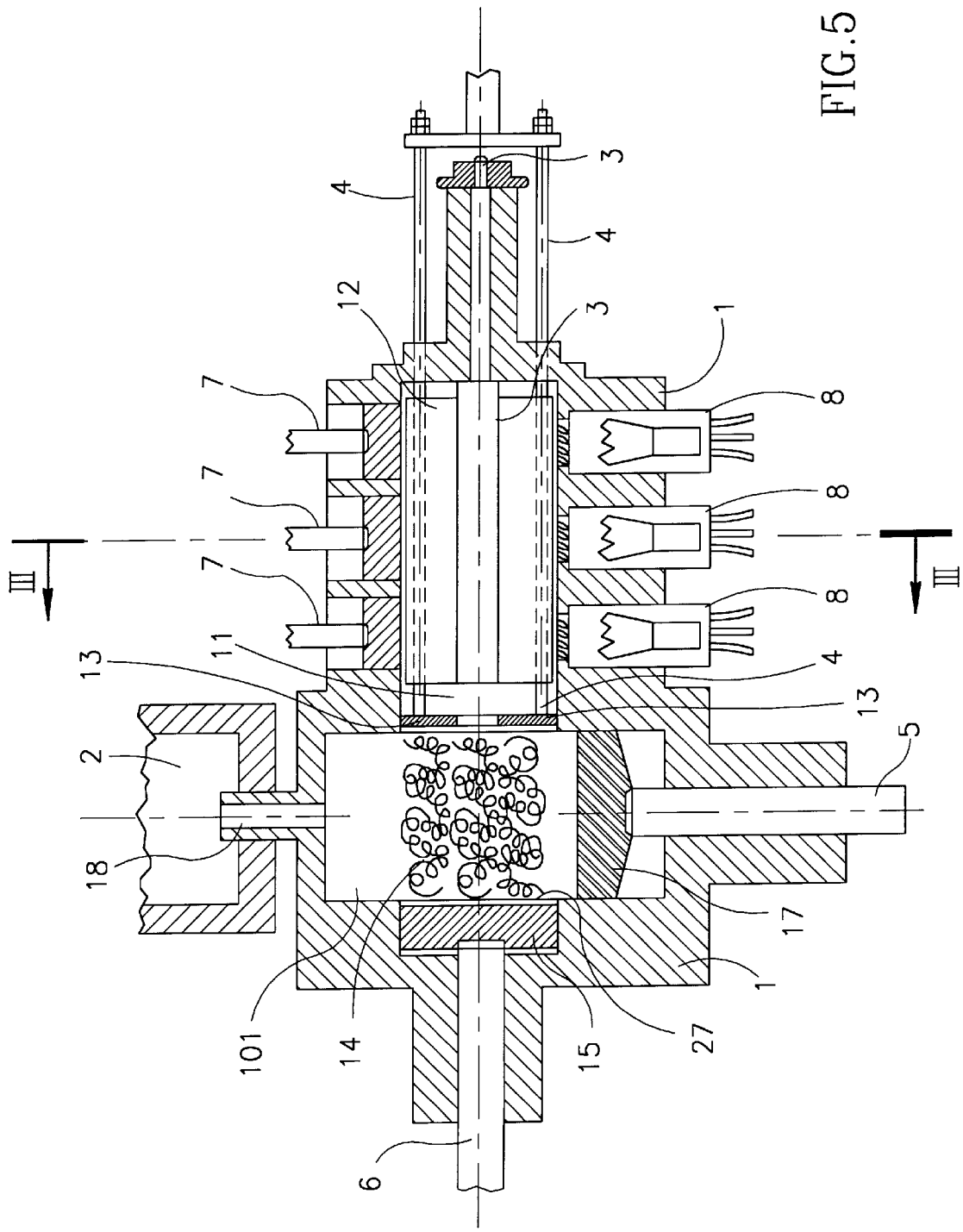
Figure 6:
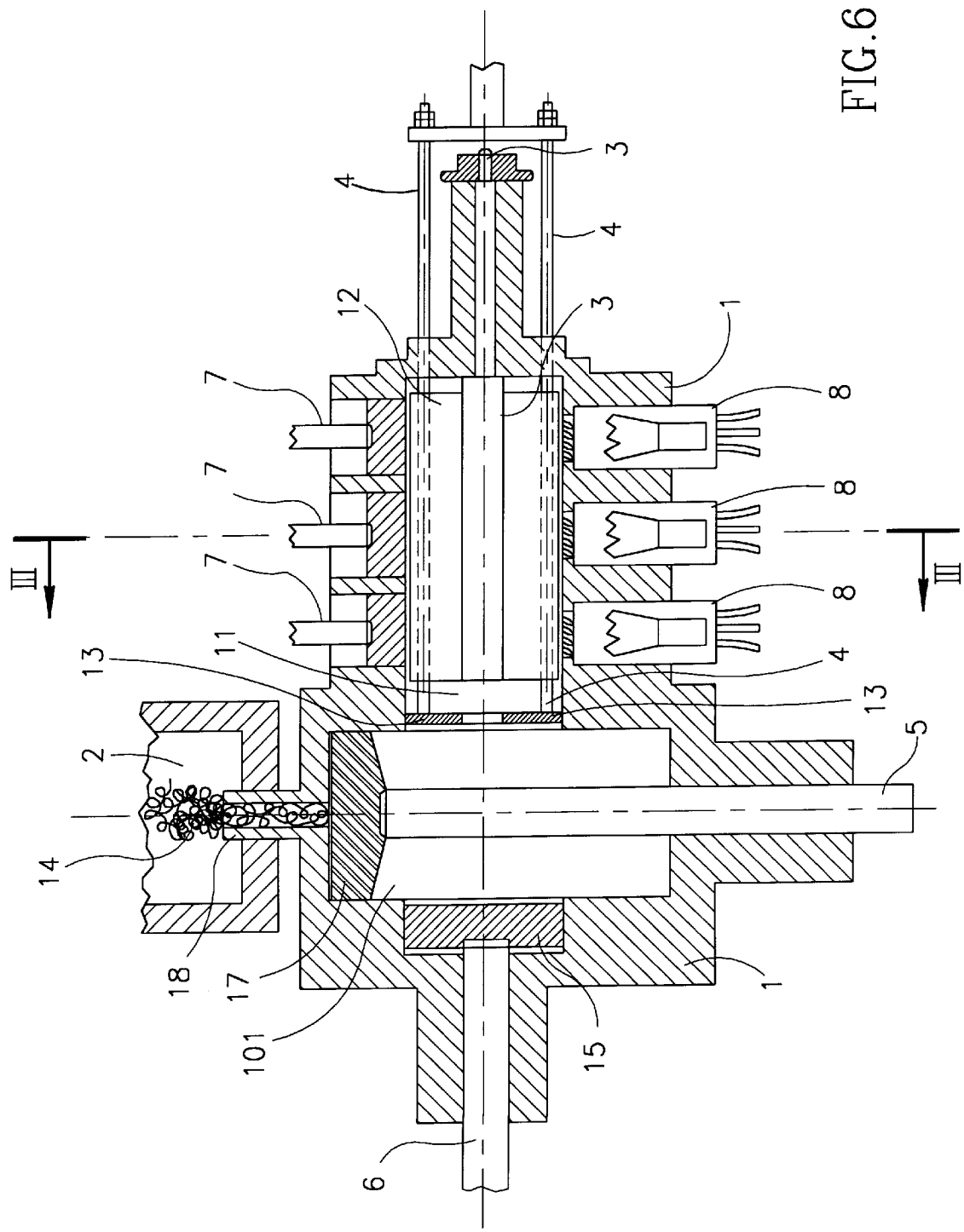

Reference is now made to FIGS. 1–6. FIGS. 1–3 schematically illustrate the apparatus for producing the superabsorbent foam of the present invention. FIGS. 4–6 are schematic cross-sectional illustrations of the apparatus in a first, second and third working positions, respectively.

The apparatus, generally referenced 100, comprises a reactor 1 having a reaction volume 11 (FIG. 3) defined by two pistons 13 and 15 in a first working position (FIG. 4). In the reaction volume 11, the superabsorbent foam is formed from a suitable reaction mixture.

The apparatus 100 also comprises a receiving chamber 101 for receiving the superabsorbent foam after its production in reactor 1. The superabsorbent foam is then pushed out of receiving chamber 101, through outlet 18, into a collection chamber 2, for further processing.

In accordance with a preferred embodiment of the present invention, the reactor 1 and the receiving chamber 101 are generally perpendicular.

As best seen in FIG. 3, a stirring unit 103 is operative within the reaction volume 1 to rotate and stir the reaction mixture 14 from which the superabsorbent foam is formed. Stirring unit 103 comprises a shaft 3 and stirring blades, generally designated 12.

As best seen in FIG. 4, apparatus 100 also comprises a piston assembly which includes a first piston arrangement, comprising at least one piston 13 operated by connecting shafts 4 and a second piston arrangement, comprising a second piston 15 moved by a connecting shaft 6. The first piston 13 and the second piston 15 define the reaction volume 11 within the reactor 1 and operate to displace the formed superabsorbent foam from its first location in the reaction volume 11 (FIG. 4) to a second location in the receiving chamber 101 (FIG. 5). A third piston arrangement comprises a shaft 5 which is operative to move a piston 17 within the receiving chamber 101, for displacing the formed superabsorbent foam from its second location in the receiving chamber 101, via outlet 18, to a collection chamber 2 (FIG. 6).

An object of the present invention is to apply mechanical waves to the reaction mixture, thereby forming the superabsorbent foam. According to a preferred embodiment of the present invention, there is provided a source of sonication energy which operates to apply ultrasound and audible waves of a desired wavelength, amplitude and shape to the reaction mixture. The source of sonication energy may include a transducer 7 molded to the wall of the reactor 1 and forming part thereof, or any other suitable element for providing sonication energy known in the art, as described for example in *"Practical Sonochemistry"* by Timothy J. Mason, published by Ellis Hormood Ltd. in 1991, in particular in section 4.3 thereof.

Apparatus 100 also comprises a plurality of Ultra Violet (UV) light sources 8 which operate to apply UV light to the reaction mixture in order to induce cross linking reactions therein. According to a preferred embodiment of the present invention, the superabsorbent foam is a collagen based solution capable of forming cross links therebetween. The application of UV energy may be useful in medical application where due to potential unfavorable action of cross linking reagents they are not useable due to their potential health risk, i.e. their unfavorable crosslinking with the body tissues.

Apparatus 100 also comprises a plurality of openings 9 and 10 forming channels in the wall of the reactor 1. The openings 9 and 10 operate as inlets and/or outlets for a blowing agent. The blowing agent is preferably a suitable inorganic gas such as, air, nitrogen and carbon dioxide; or an organic gas or volatile liquids, such as aliphatic hydrocarbons, preferably having up to seven carbon atoms in their chain and, halogenated aliphatic hydrocarbons, preferably fluorinated hydrocarbons with up to four carbons in their chains. The blowing agent is introduced into the reactor 1 by any suitable system capable of increasing and decreasing pressure in the reaction volume 11. For example, the blowing agent may be stored outside the reactor, under pressure in a tank having a system of tubes and cocks (not shown). By periodically and synchronously opening and closing the cocks, pressure pulses are generated within the reaction volume 11, thereby causing multiple disruptions of the foam cells walls and formation of an extensively branched porous system in the solidifying foam which leads to improved absorbing qualities.

As best seen in FIG. 3, the openings 9 and 10 are preferably oblique with respect to that of the blades 12 so as to minimize leakage of foam with the blowing agent from the reactor chamber 11.

Reference is now specifically made to FIGS. 4–6, which illustrate the apparatus 100 in three different operating positions.

In the first position (FIG. 4), piston 13 and piston 15 define the reaction volume 11 wherein the solidification of the reaction mixture 14 takes place.

In the second position (FIG. 5), after formation of the foam from the reaction mixture 14, piston 15 is recessed into its housing 27 allowing piston 13 to push the foam 14 into receiving chamber 101. Housing 27 is configured to allow piston 15 to be recessed, thereby enabling piston 17 to move freely within the receiving chamber 101 so as to force the foam 14 through outlet 18 into the collection chamber 2.

It is a particular feature of the present invention that pistons 15 and 17 operate substantially within the same volume. Thus, the formed superabsorbent foam may be displaced, within the reactor 1, with a minimum of compression deformation, thereby, preserving the porous structure of the solidified superabsorbent foam or reaction mixture 14.

Reference is now made to FIGS. 7–10 which illustrate four alternative stirring units 103 of the apparatus 100. According to a preferred embodiment of the present invention, the shape of the stirring unit 103 complements the shape of piston 13, 13A and 13B so as to enable displacement of pistons 13, 13A and 13B in the reactor 1.

Figure 7:
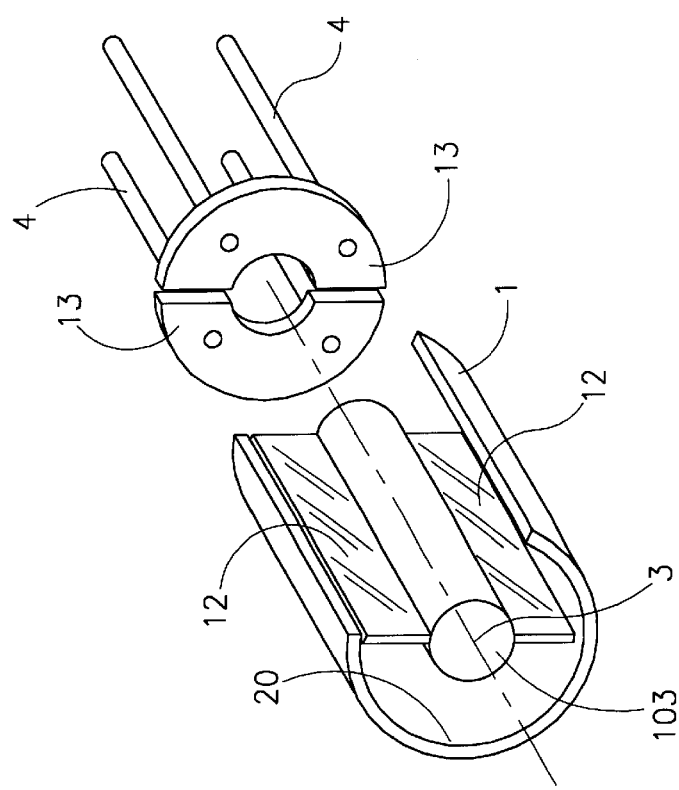

FIG. 7 illustrates two planar blades 12, each blade having one edge fixed to the cylindrical shaft 3 while the other edge is in close proximity to the reactor wall 20. The sources applying mechanical waves to the reaction mixture 14, such as transducers 7, are located adjacent to the reactor wall 20 so as to increase the efficiency and formation of pores in the reaction mixture 14. In a cylindrical reactor, the rotation of the blades 12 distributes the applied waves throughout the formed foam and effectively transfers the foam between the area in the vicinity of the reactor wall 20 and the rest of the reactor area.

Figure 8:
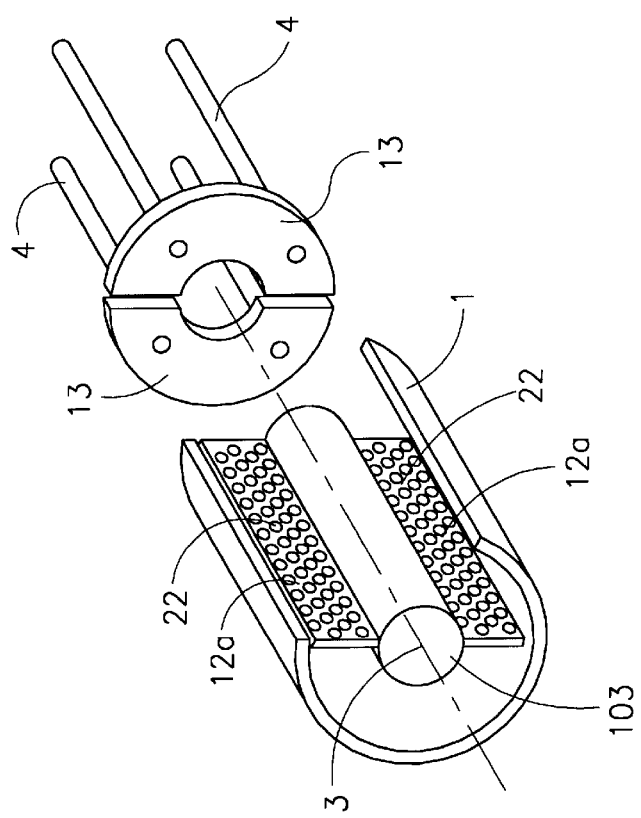
FIGS. 7, 8, 9 and 10 are schematic isometric illustrations of four alternative embodiments of blades employed in the stirring unit of the apparatus of FIGS. 1–3.
Figure 9:
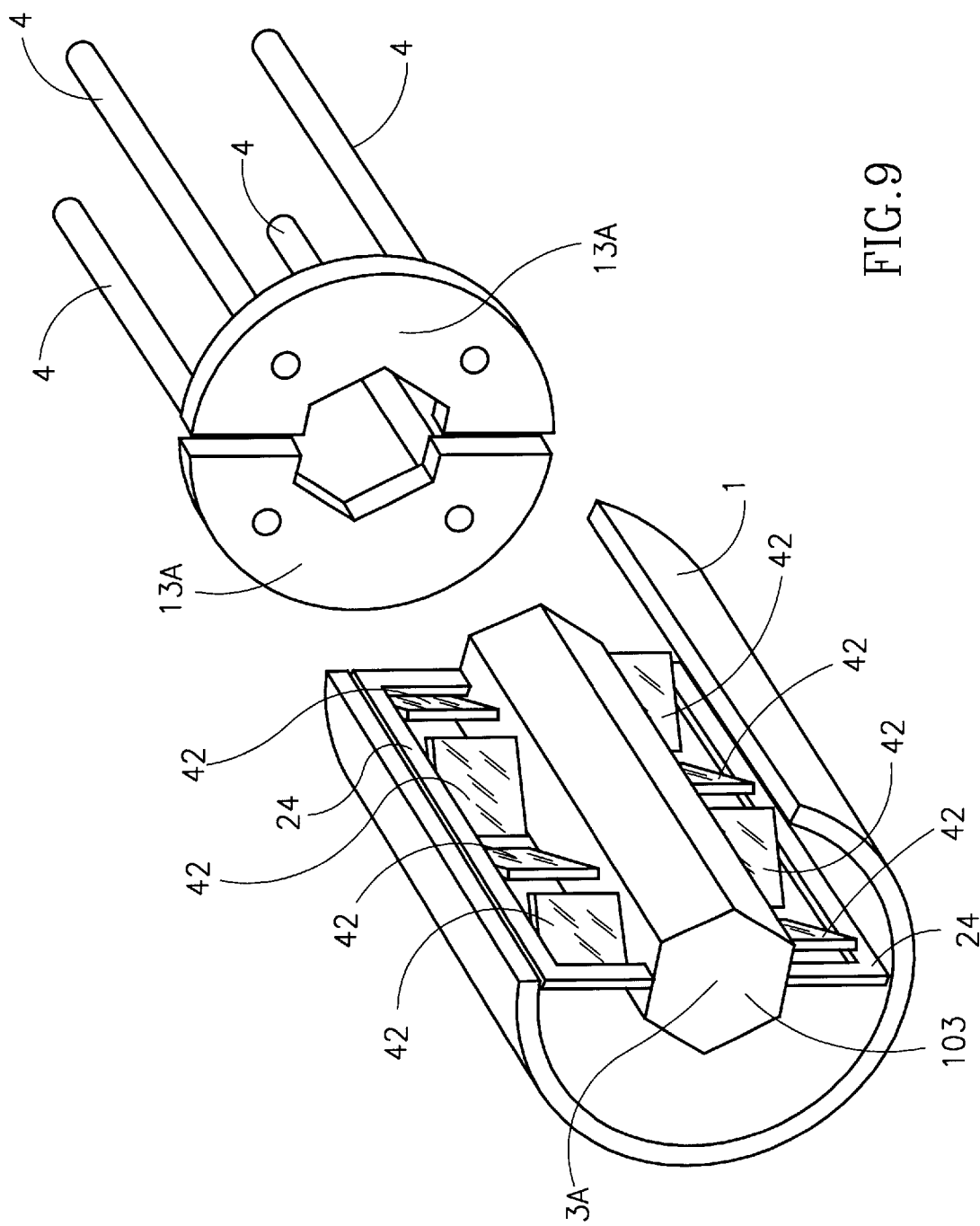
Figure 10:
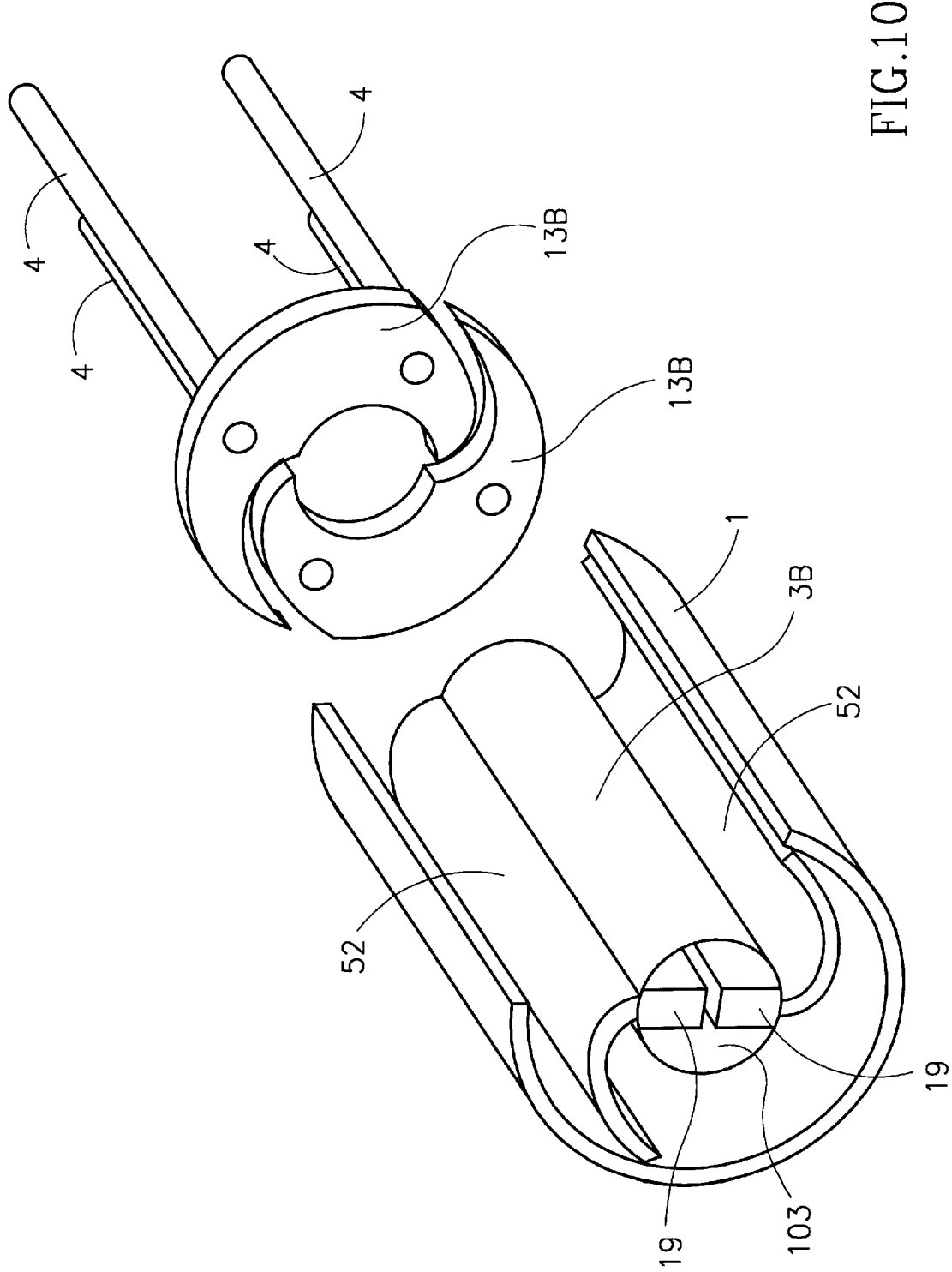

FIGS. 8–10 illustrate alternative stirring units for the capable and efficient transfer of foam within the reaction volume 11.

In the embodiment of FIG. 8, the blades 12a have multiple openings 22, respectively, arranged therethrough in a staggered fashion. As described with respect to FIG. 7 hereinabove, the increased turbulence and vortexing caused by the rapid rotation of the blades transfers wave motion throughout the foam.

FIGS. 9 and 10 illustrate another two preferred embodiments of the stirring unit 103. The stirring unit of FIG. 9 comprises a frame 24 having mounted therein a plurality of movable blade sections 42, on each side of the central shaft 3. Each of the blade sections 42 is capable of independently rotating around an axis coinciding with the plane of the frame 24. Preferably, the blade sections 42 are configured in a zig-zag like configuration as shown in FIG. 9.

In the illustrated embodiment of FIG. 9, the shaft 3A on which the blade sections 42 are mounted is of hexagonal form to enable rotation of blade sections 42 about a planar surface. On completion of the reaction cycle and solidification of the foam, the blade sections 42 can be retracted within the plane of the frame 24, so as not to interfere with the movement of the piston 13A. The solidified foam can then be easily displaced by piston 13A and expelled from reaction chamber 11 into receiver chamber 101.

The blade sections 42 can be rotated by any suitable mechanism, such as a cam arrangement in which the rod-like protrusions of the blade sections 42 within the hollow interior of the shaft 3A (not shown) serve as cam-operated driven members.

FIG. 10 shows a stirrer device with curved blades 52. The curvature of the blades 52 is characterized in that the angle between the curved blade surface and a plane, parallel to a tangent plane to the cylindrical shaft 3B at the line of blade fixing, continuously decreases from 90 degrees at the shaft surface to about 5–10 degrees near the side wall of the reaction chamber.

In order to prevent congregation of congealed foam fractions, which are continuously formed and accumulated near the wall of reactor 1 in the course of foam solidification, and to provide more uniform action of physical energy on the reactor content, the near-wall layers are periodically disturbed by oscillations of the blades 52 provided with a system of coils 19, placed in the interior of the hollow shaft 3B, as shown in FIG. 10, and connected with the rod-like protrusions of the blades 52 into the shaft interior.

It will be appreciated that this type of blade curvature affords a differential rate of transfer of the contents from the center of the reactor to areas on the periphery, which proximate to the applied wave sources or transducers 7. The closer the contents are to the center of the reactor, the more efficiently they are transferred to the reactor's side wall.

It will be appreciated that the apparatus 100 has numerous advantages for forming superabsorbent foams, a few of which are described hereinbelow.

The apparatus 100 provides efficient exposure of the reaction mixture to different kinds of physical energy including those whose propagation in non-homogenous media is deficient since the content of the reaction mixture is transferred by the stirring unit from the center of the reaction volume 11 to its periphery where the wave sources are located.

Moreover, the apparatus 100 is characterized by the efficient mass transfer within the reactor 1, of the reactor contents, having a wide range of viscosity values up to solidification and including mixtures whose viscosity increases during the reaction.

Additionally, the apparatus 100 enables the use of external and/or internal blowing agents and the possibility of inducing pressure pulses of blowing agent within the reaction volume.

The apparatus 100 provides efficient extrusion of the solidified superabsorbent foam from the reaction volume 11 to the receiving volume 101 and the collection volume 2 while substantially preserving the porous structure of the solidified foam.

A preferred compound for forming the superabsorbent foam of the present invention is collagen. The swelling rate of crosslinked collagen in water depends on its crosslinks density, the lower the density (which is determined by the crossliner concentration) the higher the swelling rate (WAC). A set of collagen samples with different crosslinks densities were prepared and the effect of a physical treatment on collagen samples with different values of basic absorption capacity was studied. Collagen was crosslinked with glutaraldehyde (GA). Collagen-GA systems were gelled within a time frame of 2–20 min (depending primarily on GA concentration). These time intervals were convenient for exposing the reaction mixtures to physical factors leading to solidification in the course of the reaction.

The preferred method for preparing collagen based superabsorbent foam comprises the application of ultrasound and/or audible waves to the reaction mixture with or without additional wave application, pressure alternation and compression as described in more detail hereinbelow.

The following examples illustrate without limitation certain aspects of the present invention.

EXAMPLE 1

This example illustrates the effect of sonication of a reaction mixture on absorption properties of loosely crosslinked collagen samples.

Experimental Conditions

Experiments were conducted using a conventional laboratory Branson sonifier-450 as a source of vibrational energy and collagen crosslinked with glutaraldehyde (GA) as a test-reaction mixture.

A Branson sonifier 450 provides a constant oscillation frequency of 20 Khz. A horn with a ½" probe was used. At the end of the probe a stainless steel disc (diameter 35 mm, thickness 1 mm) was mounted. The reaction mixture (about 25 ml) was introduced into a cylindrical vessel with a plane bottom (internal diameter 50 mm) with a magnet rod therein for stirring. A disc at the end of the sonifier probe was placed at the reaction mixture/air interface so as to imitate the sonification of the reaction mixture as described with respect to the preferred embodiment of the invention.

An intermittent sonication scheme was used, that is, stirring and sonication were switched on in turn, for periods of 10 seconds at a time. Sonication caused formation of a fluffy fine-cell foam from the reaction mixture containing surfactants (described hereinbelow).

The foam was progressively solidified in the course of the reaction according to development of the crosslinking process. The intermittent sonication-stirring treatment was continued until the foam has been solidified to such an extent that its porous structure was preserved on subsequent storage at room temperature for the further development of crosslinking process. This solidification time was about 4–5 min for the reaction mixture used, the composition of which is described hereinbelow) and GA concentration 0.30% v/v (loosely crosslinked collagen samples).

Temperature of the reaction mixture was controlled with a thermocouple facility and did not exceed 42–45° C. due to using the intermittent sonication and pulsed mode scheme (duty cycle 40%. at output control of 4–5).

Composition of the Reaction Mixture

The reaction mixture contained a water-soluble collagen (Serva, Heidelberg, Germany) as a major component and some amount of gelatin (Mata Food Industries, Hadera, Israel). Other chemicals were from Sigma Chem. Co (St. Louis, U.S.A.). Additives which were used in the reaction mixture surfactants included: cationic benzalkonium chloride (known as an efficient disinfectant) and non-ionic Tween-20 (widely used for pharmaceutical applications). Glycerol was used as a plasticize, and phosphates and sodium chloride for buffering and isotonicity.

The reaction mixture used in Example 1 was made in a following way: Initially 7% (w/v) stock solutions of collagen, gelatin, Tween 20 and glycerol, each in 0.2% solution of benzalkonium chloride in phosphate-buffered saline, Ph 7.4 (BC/PBS), were prepared. Then the stock solutions were mixed in the following proportion: 15 ml of collagen, 5 ml of gelatin, 1.25 ml of Tween 20 and 1.25 ml of glycerol and 2.5 ml of BC/PBS to provide a total volume of the reaction mixture of 25 ml.

Preparation of Samples 25 ml of prepared reaction mixture were placed in a reaction vessel, as described hereinabove with respect to the preferred embodiment of FIGS. 1–10, a magnetic stirrer was switched on and 2.78 ml of 3% of water solution of GA was added to the reaction mixture to give final concentration of GA in the reaction mixture of 0.30% and the intermittent stirring-sonication treatment was performed according to the scheme given above until the foam was solidified to a required consistency. After treatment the foam was stored for an hour at room temperature to allow further development of collagen and gelatin crosslinking. Then, the foam was placed into a vacuum oven at 40° C. for drying overnight. The reference ("conventional") samples were prepared in the same way and in the same vessel except the sonifier was not switched on.

Measurement of Swelling Rates (WAC)

A dry sample was carefully weighed (dry weight) and then placed into a vessel with PBS in a thermostated bath at 37° C. for certain time intervals. At the end of each time interval the sample was removed from PBS, blotted gently with filter paper to remove excess of water on the sample surface and weighed (wet weight). The difference between the wet and dry weights gives the amount of water absorbed by the sample. The water absorption capacity of the sample was expressed as amount of grams of water absorbed per gram of dry sample.

Figure 11:
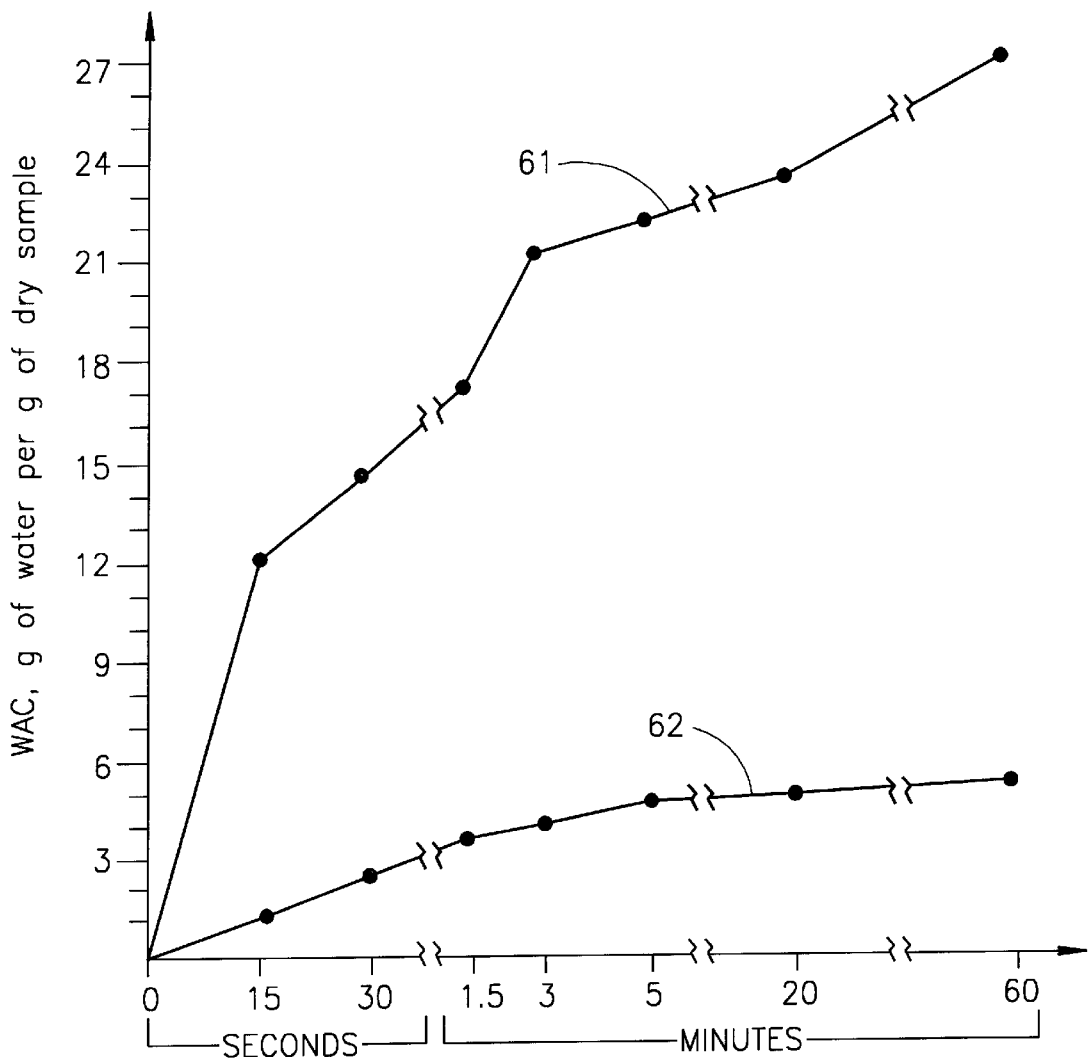
FIG. 11 is a graph illustrating the improved water-absorbent capacity of a collagen foam of the present invention, in three different time ranges of swelling.

Reference is now made to FIG. 11, which is a graph illustrating WAC, i.e., the swelling capacity (Y-axis) of the superabsorbent foam of the present invention (curve 61) compared with that of prior art conventional collagen sample (curve 62) for three time ranges (X-axis). Swelling rates of loosely crosslinked (0.30% of GA) collagen samples were prepared by using sonication treatment. The effect is illustrated in curve 61. A conventional collagen sample, that is without sonication is illustrated in curve 62. The time scale covers intervals (from seconds to 60 minutes).

As clearly seen in FIG. 11 the swelling of the loosely crosslinked collagen samples prepared in accordance with the method of the present invention employing sonication (curve 61) is higher in all time ranges than the WAC of the same collagen without wave application (curve 62). It is clearly seen that the swelling of the superabsorbent foam of the present invention is superior both at shorter and longer times.

The following examples illustrate the preparation of superabsorbent foam. Collagen was used as the example in the experiments. These illustrations are by way of example only and are not to be construed as in any way limiting to the present application.

More specifically, the "sonicated" sample swells faster and more than the "conventional" sample. The difference is particularly large at the initial stage of swelling (more than 9 times higher as compared with a conventional sample within first 15 seconds). After an hour of swelling, the "sonicated" sample exceeds the "conventional" one by a factor of about 5.5 and its WAC reaches as much as 27 grams of absorbed water per 1 gram of dry sample.

EXAMPLE 2

Effect of sonication of a reaction mixture on absorption properties of strongly crosslinked collagen samples.

Strongly crosslinked collagen samples ("sonicated" and "conventional") were prepared in the same way as the loosely crosslinked samples as described in Example 1, except that a much larger GA concentration of 1.75%, instead of 0.35%, was used. Strongly crosslinked samples absorb significantly less water than loosely crosslinked samples. However in this case sonication of the reaction mixture also markedly increases swelling rates (Table 1).

TABLE 1

Swelling rates (grams of water per gram of dry sample) of sonicated and conventional strongly crosslinked collagen samples at different swelling times

| Sample | Swelling time | | |
|---|---|---|---|
| | 1 min | 5 min | 1 hour |
| Sonicated | 1.71 | 3.98 | 4.62 |
| Conventional | 0.31 | 0.90 | 1.25 |

Swelling rates of sonicated samples exceed those of conventional samples by a factor of 5.5 after 1 min and by factors more than 3.5 after 5 min and 1 hour.

EXAMPLE 3

Swelling of sonicated and conventional collagen samples in a protein solution.

Sonicated and conventional collagen samples were prepared as in the Example 1, except the concentration of GA was 1% to cause moderate crosslinking. Swelling of samples was performed in 7% solution of bovine serum albumin in phosphate-buffered saline (PBS) and the values of swelling rates in albumin solution were compared with those in PBS without protein. The data obtained are presented in the Table 2.

TABLE 2

Swelling rates (grams of water per gram of dry sample) of sonicated and conventional collagen samples in PBS and in 7% albumin solution in PBS

| Swelling media | Samples | Swelling time (min) | | |
|---|---|---|---|---|
| | | 2 | 5 | 15 |
| PBS | Sonicated | 5.02 | 6.43 | 7.36 |
| | Conventional | 0.76 | 1.48 | 1.82 |
| Albumin | Sonicated | 4.87 | 6.20 | 6.90 |
| | Conventional | 0.47 | 1.02 | 1.33 |

Table 2 shows that the swelling rates of the sonicated samples in a concentrated protein solution of 7% albumin are only slightly decreased (by about 3–5%) as compared with the PBS while those for conventional samples are decreased by 25–40%.

It will be appreciated that 7% albumin solution was taken since its total protein content approximately corresponds to blood serum and wound exudates and thus provide an indication for the swelling in these important biological fluids. The ability of sonicated samples to swell readily in such protein solutions is important for some medical applications, e.g. for wound dressings.

EXAMPLE 4

Effect of compression of dried sonicated collagen samples on their absorption capacity.

Figure 12:
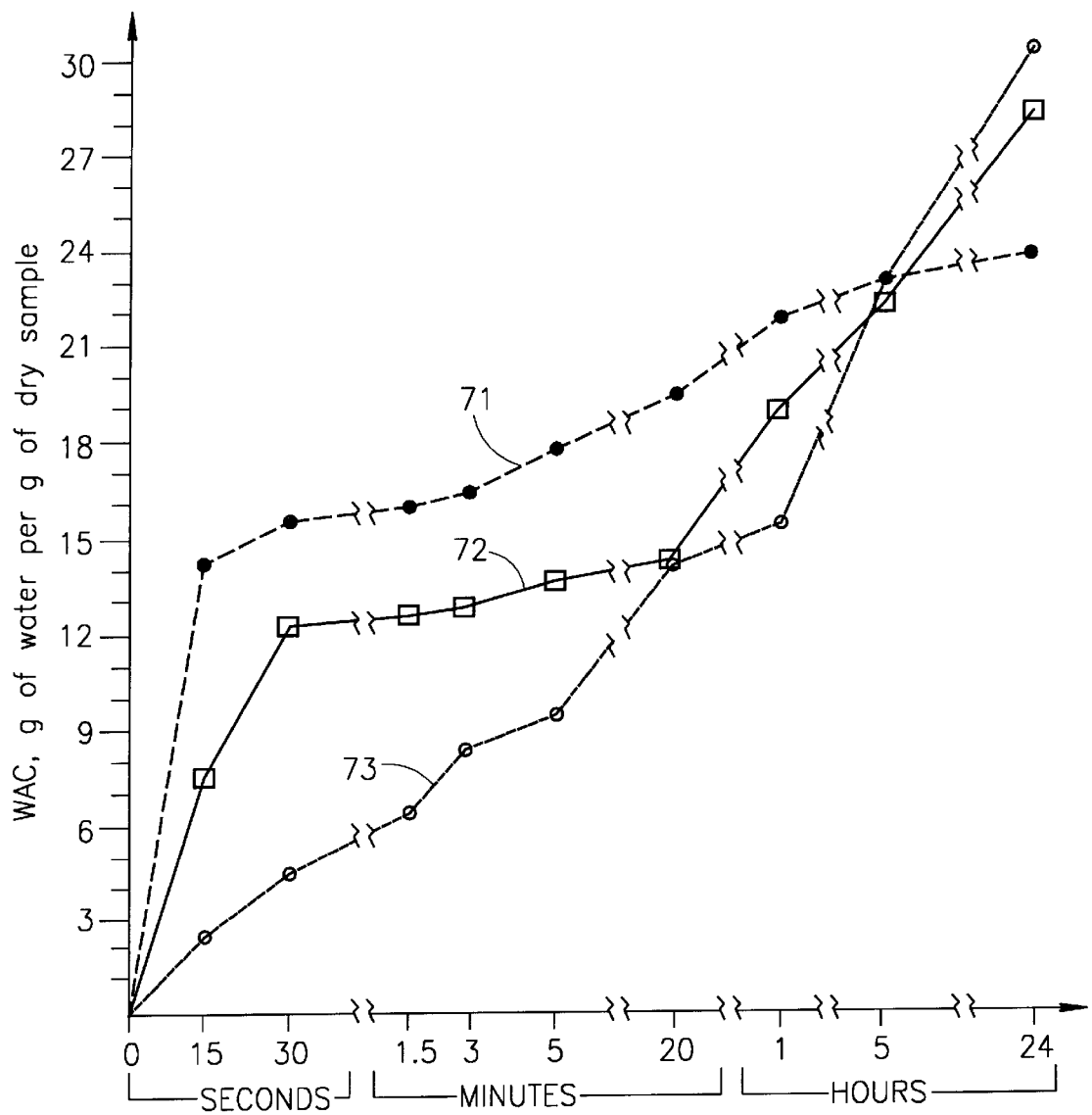
FIG. 12 is a graph illustrating the effect of compression of a collagen foam of the present invention on its water absorption capacity in different time ranges of swelling.

This experiment was performed using loosely and strongly crosslinked collagen samples prepared in the same way as in Examples 1 and 2, respectively. After drying some samples were compressed under various pressure values in the range of 10–1000 Bar and swelling rates of compressed and non-compressed samples were estimated for different time intervals as presented in FIG. 12 to which reference is now made and Table 3 for loosely and strongly crosslinked collagen samples, respectively.

A distinct difference was observed between the compression effects on the swelling rate of loosely and strongly crosslinked collagen samples prepared by means of the proposed technology. As shown on FIG. 12, compression of loosely crosslinked sonicated sample under relatively small pressure of 15 Bar (curve 72) decreases the swelling rate during the first hour of contact with PBS but further, at 5 hours, the swelling rate of compressed sample reaches that of non-compressed one (curve 71) and at 24 hours exceeds it. This effect is more pronounced under stronger pressure of 150 Bar (curve 73 on FIG. 12). At still higher pressure values of about several hundred Bar swelling rates of loosely crosslinked samples are decreased at all time intervals (not shown).

However in the case of strongly crosslinked sonicated samples (Table 3) a strong compression under value pressure such high as 1,000 Bar markedly increases the swelling rate at all time intervals studied (from 15 seconds up to 24 hours). The effect is less pronounced at relatively small pressure of 30 Bar.

TABLE 3

Swelling rates (grams of water per gram of dry sample) of non-compressed (0 Bars) and compressed at 30 and 1000 Bars strongly crosslinked collagen samples

| Pressure | Swelling Time | | | |
|---|---|---|---|---|
| Bars | 15 Sec | 3 min | 1 hour | 24 hours |
| 0 | 1.63 | 3.06 | 4.88 | 6.72 |
| 30 | 1.85 | 4.40 | 6.35 | 8.41 |
| 1,000 | 2.45 | 6.95 | 8.83 | 10.37 |

EXAMPLE 5

Effect of additional sonication of dry sonicated samples on their absorption capacity.

This experiment was performed on moderately crosslinked sonicated collagen samples prepared in the same way as in the Example 1, except that the GA concentration was 1%. Instead of compression as in the Example 4, the dry samples were sonicated. This "dry" sonication was in addition to "wet" sonication of the reaction mixture occurring during the preparation of these samples. Therefore the sonication of dry samples is called here as "additional" sonication.

For this treatment the dry sample was placed in a metal cylinder having an internal diameter of 32 mm. On the end of the ½" sonifier probe a stainless steel disc 30 mm in diameter and 3 mm in thickness was mounted. The disc was introduced into the cylinder interior containing the sample through a compressible rubber layer. The rubber layer served as a thermo-isolation unit to avoid overheating of the sample. To provide transmission of the sonication energy to the sample through the rubber layer a pressure of 6 Bar was applied to the unit having the disc at its end.

Sonication was performed in a pulse mode (duty cycle 0.3). The sample was treated with 60 pulses in total with a 2 minutes interval between the runs of 10 pulses. Temperature of the sample was controlled with a thermocouple facility between the runs of the pulses did not exceed 45–48° C.

This treatment caused a significant additional increase of swelling rates of the samples which were previously sonicated during preparation at the stage of reaction mixture as described in Example 1. These data are presented in the Table 4.

TABLE 4

Effect of additional sonication of dry samples (dry sonication), which were previously sonicated during preparation at the stage of reaction mixture (wet sonication), on their swelling rates (expressed in the same units as in the Table 1)

| Samples | Swelling rates at time intervals | | | |
|---|---|---|---|---|
| | 15 sec | 5 min | 1 hour | 24 hours |
| Wet-sonicated | 1.85 | 5.07 | 6.63 | 9.24 |
| Wet-sonicated + Dry sonicated | 2.36 | 8.25 | 10.90 | 13.69 |

The increase of the swelling rates during additional sonication of dry samples may be explained in the same way as in the case of compression of strongly crosslinked dry samples (Example 4); i.e. sonication of dry samples cause additional breakage of partitions between the pores of the sample thus causing a formation of a more branched system of intercommunicating open pores.

EXAMPLE 6

Presence of strongly and weakly bound water in samples prepared using sonication.

This example illustrates the effectivity of water absorbance by the superabsorbent foams of the present invention.

This experiment was performed on the moderately crosslinked samples prepared in the same way as in example 1 except that the concentration of GA was higher at 0.75% and their overall absorption capacity was 11.5 grams of absorbed water per gram of dry sample.

A swelled sample was placed on the nylon microporous filter (pore diameter 0.45 micron) which was put on the sintered glass filter placed on a metal grid to provide mechanical stability during compression of the swelled sample.

The experiment consisted of squeezing out water from the swelled sample by applying mechanical pressure. 6.3 grams of water (54.8%) were expelled from the sample using a relatively low pressure of about 20 Bar. Another 1.2 grams (10.4%) of water were squeezed out under high pressure of 1000 Bar. The residual 4.0 grams (approximately 34%) of water could not be squeezed from the sample even at this pressure and could only be eliminated by subsequently vacuum drying.

It will be appreciated that the residual strongly bound water is likely to be bound by molecular forces within the gel-like network comprising the partitions between pores of the sample while the weakly bound water is retained within the pores volume by capillary forces.

It will be appreciated that the present invention is not limited by what has been described hereinabove and that numerous modifications, all of which fall within the scope of the present invention, exist. For example, while the present invention has been described with respect to collagen, it is equally applicable to any material capable of forming superabsorbent foam and is not limited to any class of chemical compositions as in the prior art.

Another example is that while the present invention has been described with respect to application of ultrasonic and audible waves, any suitable waves such as non-linear waves (e.g., shock waves produced by means of electrohydraulic effect or in some other way) may be used in the formation of the superabsorbent foam.

It will be appreciated by persons skilled in the art that the present invention is not limited by what has been particularly shown and described herein above. Rather the scope of the invention is defined by the claims which follow:

What is claimed is:

1. Apparatus for forming a superabsorbent foam, the apparatus comprising:

a reactor having a reaction chamber therein for receiving a reaction mixture comprising at least one compound capable of forming a superabsorbent foam;

a receiving chamber for receiving said superabsorbent foam formed in said reaction chamber;

a stirring unit for stirring said reaction mixture, said stirring unit includes a shaft and at least one blade operating to stir said reaction mixture in said reaction chamber;

a sonication unit for applying mechanical waves selected from sonic waves and ultrasonic waves to said reaction mixture;

a control unit for repeating the operation of said stirring unit and said sonication unit a selected number of times to form said superabsorbent foam; and a first piston assembly having at least one piston for displacing said superabsorbent foam formed within said reactor from a first position within said reaction chamber to a second position within said receiving chamber.

2. The apparatus according to claim 1 wherein said at least one piston and said at least one blade are complementary in shape to enable said at least one piston to displace said superabsorbent foam from said reaction chamber.

3. The apparatus according to claim 1 further including a second piston assembly for displacing said superabsorbent foam from said receiving chamber to a collection chamber.

4. The apparatus according to claim 3 wherein said first piston assembly and said second piston assembly operate at least partly in the same volume.

5. The apparatus according to claim 1 further including channels formed in the wall of said reactor and communicating with said reaction chamber for changing the pressure in said reaction chamber and for introducing a blowing agent into said reaction mixture.

6. The apparatus according to claim 1 wherein said at least one blade of said stirring unit is an oscillating blade movable with respect to said shaft, and wherein said shaft further includes a blade oscillating mechanism operatively coupled to said oscillating blade for moving said oscillating blade with respect to said shaft to additionally perturb said reaction mixture.

7. The apparatus according to claim 1 wherein said at least one blade comprises:

a frame attached to said shaft;

at least one movable blade section rotatably attached within said frame; and a blade section rotation mechanism operatively coupled to said at least one movable blade section for rotating said at least one movable blade section within said frame.

8. The apparatus according to claim 1 further including a source of radiation for applying radiation into said reaction mixture.

9. The apparatus according to claim 8 wherein said source of radiation is selected from a source of ultraviolet radiation, a source of visible light radiation, a source of ionizing radiation and a source of microwave radiation.

10. The apparatus according to claim 7 wherein said at least one blade is a curved blade.

11. The apparatus according to claim 1 wherein said at least one blade is a perforated blade.

12. Apparatus for forming a superabsorbent foam, the apparatus comprising:

a reactor having a reaction chamber therein for receiving a reaction mixture comprising at least one compound capable of forming a superabsorbent foam;

a receiving chamber for receiving said superabsorbent foam formed in said reaction chamber;

a first piston assembly having at least one piston for displacing said superabsorbent foam formed within said reactor from a first position within said reaction chamber to a second position within said receiving chamber;

a stirring unit for stirring said reaction mixture; and a sonication unit for applying mechanical waves selected from sonic waves and ultrasonic waves to said reaction mixture.

13. The apparatus according to claim 12, wherein said stirring unit includes a shaft and at least one blade attached to said shaft and operative to stir said reaction mixture within said reaction chamber.

14. The apparatus according to claim 13 wherein said at least one piston and said at least one blade are complementary in shape to enable said at least one piston to displace said superabsorbent foam from said reaction chamber.

15. The apparatus according to claim 12 further including a second piston assembly for displacing said superabsorbent foam from said receiving chamber to a collection chamber.

16. The apparatus according to claim 15 wherein said first piston assembly and said second piston assembly operate at least partly in the same volume.

17. The apparatus according to claim 12 further including channels formed in the wall of said reactor and communicating with said reaction chamber for changing the pressure in said reaction chamber and for introducing a blowing agent into said reaction mixture.

18. The apparatus according to claim 13 wherein said at least one blade of said stirring unit is an oscillating blade movable with respect to said shaft, and wherein said shaft further includes a blade oscillating mechanism operatively coupled to said oscillating blade for moving said oscillating blade with respect to said shaft to additionally perturb said reaction mixture.

19. The apparatus according to claim 13 wherein said at least one movable blade comprises:

a frame attached to said shaft;

at least one movable blade section rotatably attached within said frame; and a blade section rotation mechanism operatively coupled to said at least one movable blade section for rotating said at least one movable blade section within said frame.

20. The apparatus according to claim 12 further including a source of radiation for applying radiation into said reaction mixture.

21. The apparatus according to claim 20 wherein said source of radiation is selected from a source of ultraviolet radiation, a source of visible light radiation, a source of ionizing radiation and a source of microwave radiation.

22. The apparatus according to claim 13 wherein said at least one blade is a perforated blade.

23. The apparatus according to claim 13 wherein said at least one blade is a curved blade.

24. The apparatus according to claim 12 further including a control unit for controlling the operation of said stirring unit, said first piston assembly and said sonication unit.

* * * * *